(12) United States Patent
Boudy et al.

(10) Patent No.: US 10,307,385 B2
(45) Date of Patent: Jun. 4, 2019

(54) GELLING FORMULATION CONTAINING KETAMINE

(71) Applicant: Assistance Publique—Hopitaux de Paris, Paris (FR)

(72) Inventors: Vincent Boudy, Paris (FR); Annick Tibi, Charenton (FR); Benoît D'Hayer, Paris (FR); Marie-Caroline Husson, Paris (FR); Sandrine Graff De Faget, La Celle Saint Cloud (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 94 days.

(21) Appl. No.: 14/423,882

(22) PCT Filed: Aug. 30, 2013

(86) PCT No.: PCT/IB2013/058165
§ 371 (c)(1),
(2) Date: Feb. 25, 2015

(87) PCT Pub. No.: WO2014/033680
PCT Pub. Date: Mar. 6, 2014

(65) Prior Publication Data
US 2015/0224070 A1   Aug. 13, 2015

(30) Foreign Application Priority Data
Aug. 31, 2012   (FR) ..................... 12 58146

(51) Int. Cl.
*A61K 9/00*   (2006.01)
*A61K 9/06*   (2006.01)
*A61K 47/34*  (2017.01)
*A61P 23/00*  (2006.01)
*A61P 23/02*  (2006.01)
*A61K 31/135* (2006.01)

(52) U.S. Cl.
CPC ............ *A61K 31/135* (2013.01); *A61K 9/006* (2013.01); *A61K 9/06* (2013.01); *A61K 47/34* (2013.01); *A61P 23/00* (2018.01); *A61P 23/02* (2018.01)

(58) Field of Classification Search
CPC ...... A61K 31/135; A61K 47/34; A61K 9/006; A61K 9/06
USPC ......................................................... 514/647
See application file for complete search history.

(56) References Cited

U.S. PATENT DOCUMENTS

| | | | | |
|---|---|---|---|---|
| 6,264,981 B1* | 7/2001 | Zhang | ................. | A61K 9/0056 424/451 |
| 8,496,957 B2* | 7/2013 | Lichter | ............... | A61K 9/0046 424/437 |
| 2003/0185761 A1 | 10/2003 | Dugger, III | | |
| 2010/0015263 A1 | 1/2010 | Lichter et al. | | |

OTHER PUBLICATIONS

Marhofer et al., "S(+)-Ketamine for Rectal Premedication in Children", 2001, Anesthesia and Analgesia, 92(1), pp. 62-65.*
Sandri et al., "An In Situ Gelling Buccal Spray Containing Platelet Lysate for the Treatment of Oral Mucositis", 2011, Current Drug Discovery Technologies, 8(3), pp. 277-285.*
Dumortier et al., "A Review of Poloxamer 407 Pharmaceutical and Pharmacological Characteristics", Dec. 2006, Pharmaceutical Research, vol. 23, Issue 12, pp. 2709-2728.*
Gao et al., "Ketamine use in current clinical practice", 2016, Acta Pharmacol Sin., 37(7), pp. 865-872.*
"Gel." Oxford Dictionaries.com, Oxford Dictionaries, https://en.oxforddictionaries.com/definition/us/gel#gel. Accessed: Aug. 2017.*
Edited by Rowe et al., (2009), Handbook of Pharmaceutical Excipients (6th ed.). London: APhA, (PhP) Pharmaceutical Press., pp. 20-22. (Year: 2009).*
National Center for Biotechnology Information. PubChem Compound Database; CID=131704328, https://pubchem.ncbi.nlm.nih.gov/compound/131704328 (accessed Jan. 7, 2019; Create Date Oct. 31, 2017). (Year: 2017).*
International Search Report and Written Opinion for Application No. PCT/IB2013/058165 dated Jan. 21, 2014.

* cited by examiner

*Primary Examiner* — My-Chau T. Tran
(74) *Attorney, Agent, or Firm* — Alston & Bird LLP

(57) ABSTRACT

A gelling formulation containing ketamine or a pharmaceutically acceptable salt thereof in water, a poloxamer and one or more pharmaceutically acceptable mucoadhesive agents is provided. Also provided is a method of using the formulation for pain treatment.

17 Claims, No Drawings

GELLING FORMULATION CONTAINING KETAMINE

FIELD

The invention relates to a gelling formulation based on ketamine, to the use thereof in the treatment of pain, and to the process for the preparation and administration thereof.

BACKGROUND

Ketamine hydrochloride or (RS)-2-(2-chlorophenyl)-2-methylaminocyclohexan-1-one, a non-competitive antagonist of medullary post-synaptic NMDA (N-methyl-D-aspartate) glutamate receptors, is a product used in France in human and veterinary anesthesia. It is characterized by a general anesthetic effect and a rapid action. It can be used as a single anesthetic agent: particularly suitable for interventions of short duration; it also makes it possible, through repeated injections or through its use by intravenous infusion, to obtain prolonged anesthesia for several hours. It can also be used either as an inducer of anesthesia before the administration of other anesthetic agents, or as a potentiator of low-potency anesthetic agents, such as nitrous oxide.

It is, moreover, used outside the context of the marketing authorization (MA), as an analgesic, in particular for the treatment of acute pain, in particular in pediatrics.

The pharmaceutical specialty products based on ketamine that are currently on the market in France are injectable solutions intended for intravenous or intramuscular administration, routes which are difficult to access in children.

SUMMARY

A new formulation which makes it possible to overcome the drawbacks of the current pharmaceutical specialty products has now been developed.

More particularly, the invention relates to a formulation based on ketamine, advantageously capable of being sprayed in the form of a liquid spray into the buccal cavity and of instantaneously gelling on contact with the mucous membranes of the mouth, and of allowing rapid and prolonged release of ketamine. Compared with a solution, the presence of a gel texture allows prolonged contact of the ketamine with the surface of the mucous membranes. This formulation offers several advantages: it is first of all easy to apply and makes it possible, on the one hand, to increase the exchange surface in the buccal cavity, when it is sprayed in liquid form, and, on the other hand, to increase the amount of time the active ingredient is present in the buccal cavity by virtue of its gel form; it makes it possible to obtain better bioavailability of the ketamine; it can, moreover, be easily prepared and packaged so as to be stored under sterile conditions, and may contain no preservatives. Finally, this formulation makes it possible to give first aid rapidly, safely and economically, in particular in emergencies in children.

Thus, according to a first aspect, the invention relates to a gelling formulation comprising ketamine or a pharmaceutically acceptable salt thereof, a poloxamer, and water.

DETAILED DESCRIPTION

For the purposes of the present description, the term "gelling formulation" is intended to mean a formulation capable of gelling, in particular in which the concentration of the poloxamer(s) is sufficient to allow the aqueous solution to gel at a given temperature, in particular on contact with the skin, in particular the mucous membranes of the buccal cavity, in particular the mucous membranes of the tongue and of the cheeks.

Ketamine is the compound having the following structure:

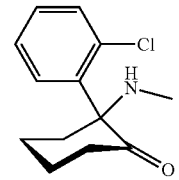

According to one preferred embodiment, the gelling formulations according to the present application comprise a pharmaceutically acceptable salt of ketamine, in particular ketamine hydrochloride.

The ketamine can be used in its racemic form, or in an enantiomerically enriched form. Preferably, the S-(+) enantiomer of ketamine, also called esketamine, or a pharmaceutically acceptable salt thereof, is used.

The formulations according to the present application preferably comprise from 2 to 20 g/100 ml of ketamine or of a pharmaceutically acceptable salt thereof, more preferentially approximately from 2 to 10 g/100 ml of formulation, and in particular approximately 8 g/100 ml of ketamine.

As used herein, the term "poloxamer" denotes a copolymer organized as a triblock copolymer comprising or consisting of a central chain of polyoxypropylene (also called polypropylene glycol, POP) grafted on either side with a chain of polyoxyethylene (also called polyethylene glycol, POE). Poloxamers are generally denoted by the letter "P" (for poloxamer) followed by three numbers: the first two numbers multiplied by 100 give the molecular weight of the polyoxypropylene core, and the final number multiplied by 10 gives the percentage polyoxyethylene content. By way of example, P407 corresponds to a poloxamer of which the polyoxypropylene core has a molecular weight of 4000 g/mol and a polyoxyethylene content of 70%.

The poloxamers that are of use according to the invention are thermosensitive poloxamers which, depending on their concentration in solution, are in the liquid state at ambient temperature, and in particular between +8° C. and +33° C., and in the gel state at a temperature greater than or equal to the gelling temperature ($T_g$), in particular under physiological conditions, and in particular between +30° C. and +40° C.

The gelling temperatures of the poloxamers ($T_g$) can be determined according to methods which are conventional or are available in reference works such as the *Handbook of Pharmaceutical Excipients*.

More particularly, these poloxamers are present in a concentration sufficient in the aqueous solution of ketamine or of a pharmaceutically acceptable salt thereof to allow gelling thereof when the temperature is greater than or equal to their gelling temperature ($T_g$), in particular under physiological conditions.

Preferably, the formulation gels at a temperature between +30° C. and +37° C., more preferentially on contact with the skin or the mucous membranes, in particular at a temperature between +31° C. and +34° C.

The formulations according to the present application generally comprise from 15 to 20 g/100 ml of poloxamer, preferably from 16 to 19 g/100 ml. As an example, mention may in particular be made of poloxamer 407, poloxamer 188, or a mixture thereof.

The formulations according to the present application may also comprise one or more pharmaceutically acceptable excipients chosen from mucoadhesive agents, taste-masking agents, acidic agents, basic agents, preservatives and sodium chloride or potassium chloride.

As examples of a mucoadhesive agent, mention may in particular be made of alginates (for example, Kelton®, Manugel LBA®, Satialgine®), gellan gums (for example, Gelzan®), xanthan gums (for example, Satiaxane®), gum tragacanth, karaya gum, carrageenans (for example, Satiagel®), pectins, chitosans (for example, Chitoclear®), hyaluronic acid and salts thereof, acrylic acid polymers (for example, Carbopol®, Noveon®), copolymers of methyl vinyl ether and of maleic acid (for example, Gantrez®), poly(N-vinyl-pyrrolidone) and derivatives thereof (for example Kollidon 90F®), and also cellulose-based derivatives (HPMC, HPC, HEC, NaCMC).

As examples of a taste-masking agent, mention may in particular be made of low-calorie sweeteners, such as sucralose, and stevia and more particularly its extract, rebaudioside A at 97% (for example, Rebaten 97®). Flavors such as tutti frutti, strawberry, raspberry, caramel, cola or citrus (orange, lemon) may also be used to mask the taste of the formulation.

As examples of an acidic agent, of use for adjusting the pH of the solution, mention may in particular be made of hydrochloric acid, acetic acid and boric acid.

As examples of a basic agent, also of use for adjusting the pH of the solution, mention may be made of sodium hydroxide and potassium hydroxide solutions.

As examples of a preservative, mention may in particular be made of sorbic acid and boric acid.

According to one embodiment, the formulations of the invention comprise approximately 17 g/100 ml of poloxamer 407, and between 0.04 and 2 g/100 ml of mucoadhesive agent such as, by way of example, sodium alginates, xanthan gums or carrageenans.

Advantageously, the formulations according to the invention are sterile and can be prepared by sterilizing filtration, by radiosterilization, or else under aseptic conditions. More particularly, this solution can be prepared and/or stored under sterile conditions in a bottle equipped with a suitable sprayer.

According to another aspect, the invention relates to a pharmaceutical composition comprising or consisting of a gelling formulation as defined above.

According to yet another aspect, the invention relates to a gelling formulation as defined above, for use in the treatment of pain, intended in particular to be administered in the buccal cavity, sublingually.

Preferably, the formulation according to the present application is sprayed into the buccal cavity, and instantaneously forms a gel on the area of application, which is preferentially sublingual.

According to another aspect, the invention relates to a method for preparing a gelling formulation as defined above, said method comprising the steps of:
i) dissolving, under cold conditions, the poloxamer in water, in particular at a temperature between +8° and +16° C.;
ii) adding and dissolving one or more mucoadhesive agents, preferably at a temperature between +40° C. and +70° C.;
iii) adding and dissolving ketamine or a salt thereof to and in the solution obtained in step i), preferably at ambient temperature, in particular at a temperature between +15° and +25° C.; and
iv) recovering the formulation obtained.

According to one alternative, the method comprises the steps of:
i) dissolving ketamine or a salt thereof in water, preferably at ambient temperature, in particular at a temperature between +15° C. and +25° C.;
ii) adding and dissolving one or more mucoadhesive agents, preferably at a temperature between +40° C. and +70° C.;
iii) adding and dissolving the poloxamer to and in the solution obtained in step i) cooled beforehand, in particular at a temperature between +8 and +16° C.; and
iv) recovering the formulation obtained.

Definitions

As used in the present description, the term "approximately" refers to a range of values of ±10% of a specific value. By way of example, the expression "approximately 17 g/100 ml" comprises the values of 17 g/100 ml±10%, i.e. the values from 15.3 g/100 ml to 18.7 g/100 ml.

For the purposes of the present description, the ratios x g/100 ml refer to ratios by weight relative to 100 ml of final formulation in the liquid state, unless otherwise indicated.

As intended herein, the value ranges in the form of "x-y" or "from x to y" or "between x and y" include the limits x and y and also the whole numbers included between these limits. By way of example, "1-6", or "from 1 to 6" or "between 1 and 6" denote the whole numbers 1, 2, 3, 4, 5 and 6. The preferred embodiments include each whole number taken individually within the value range, and also any sub-combination of these whole numbers. By way of example, the preferred values for "1-6" can comprise the whole numbers 1, 2, 3, 4, 5 6, 1-2, 1-3, 1-4, 1-5, 2-3, 2-4, 2-5, 2-6, etc.

EXAMPLES

Example 1: Preparation of Gelling Formulations Based on Ketamine Hydrochloride (Method A)

18 g of poloxamer 407 (Kolliphor P407®, BASF) were dissolved under cold conditions, in 100 ml of water, then 9.23 g of ketamine hydrochloride (i.e. 8 g of ketamine) were added and dissolved while stirring for approximately one hour.

The solution (F1) obtained gels on contact with the mucous membranes of the buccal cavity.

The formulations F2 to F7 reported in table I below were prepared according to the same procedure. As regards the formulations F3 and F4, the mucoadhesive agent (alginate) was added beforehand to the solution of poloxamer before addition of the ketamine at a temperature between +40° C. and +70° C.

TABLE I

| Formulation No. | Ketamine (g/100 ml) | Lutrol ® F127 (Poloxamer 407) (g/100 ml) | Manugel ® LBA (Alginate) (g/100 ml) |
|---|---|---|---|
| F1 | 8 | 18 | — |
| F2 | 8 | 19 | — |
| F3 | 8 | 19 | 0.5 |
| F4 | 8 | 19 | 1 |
| F5 | 2 | 15 | |
| F6 | 4 | 15 | |
| F7 | 6 | 15 | |

Example 2: Preparation of a Gelling Formulation Based on Ketamine Hydrochloride (Method B)

9.23 g of ketamine hydrochloride (i.e. 8 g of ketamine) were dissolved in approximately 100 ml of water while stirring.

18 g of poloxamer 407 (Kolliphor P407®, BASF) were then dissolved under cold conditions.

The solution obtained gels on contact with the mucous membranes of the buccal cavity.

The invention claimed is:

1. A liquid gelling formulation comprising ketamine or a pharmaceutically acceptable salt thereof, 15 to 20 g/100 ml of a poloxamer, from 1 to 2 g/100 ml of at least one pharmaceutically acceptable mucoadhesive agents, and water.

2. The liquid gelling formulation as claimed in claim 1, wherein the ketamine is the S-(+) enantiomer of ketamine or a pharmaceutically acceptable salt thereof.

3. The liquid gelling formulation as claimed in claim 1, comprising from 2 to 20 g/100 ml of ketamine or of a pharmaceutically acceptable salt thereof.

4. The liquid gelling formulation as claimed in claim 1, comprising from 16 to 19 g/100 ml of poloxamer.

5. The liquid gelling formulation as claimed in claim 1, wherein the poloxamer is chosen from poloxamer 407, poloxamer 188, or a mixture thereof.

6. The liquid gelling formulation as claimed in claim 1, also comprising one or more pharmaceutically acceptable excipients chosen from taste-masking agents, acidic agents, basic agents, preservatives, sodium chloride and potassium chloride.

7. The liquid gelling formulation as claimed in claim 1, characterized in that the gelling formulation as a whole is sterile.

8. The liquid gelling formulation as claimed in claim 1, characterized in that it is intended for sublingual administration.

9. The liquid gelling formulation as claimed in claim 1, characterized in that it is intended to be sprayed in the form of a liquid spray into the buccal cavity.

10. A pharmaceutical composition comprising formulation as claimed in claim 1.

11. A method of treating an individual suffering from pain comprising the step of administering the liquid gelling formulation of claim 1.

12. The method as claimed in claim 11, wherein the formulation is sprayed in the form of a liquid spray into the buccal cavity.

13. A method for preparing a liquid gelling formulation as claimed in claim 1, said method comprising the steps of:
   i) dissolving, under cold conditions, the poloxamer in water;
   ii) adding and dissolving one or more mucoadhesive agents;
   iii) adding and dissolving ketamine or a salt thereof to and in the solution obtained in step i), at ambient temperature; and
   iv) recovering the formulation obtained.

14. A method for preparing a liquid gelling formulation as claimed in claim 1, said method comprising the steps of:
   i) dissolving ketamine or a salt thereof in water, at ambient temperature;
   ii) adding and dissolving one or more mucoadhesive agents at a temperature between +40° C. and +70° C.;
   iii) adding and dissolving the poloxamer to and in the solution obtained in step i) cooled beforehand, at a temperature between +8° C. and +16° C.; and
   iv) recovering the formulation obtained.

15. The method of claim 14, wherein the step of dissolving ketamine or a salt thereof in water is at a temperature between +15° C. and +25° C.

16. The method of claim 13, wherein the step of dissolving the poloxamer in water is at a temperature between +8° C. and +16° C., the step of adding and dissolving one or more mucoadhesive agents is at a temperature between +40° C. and +70° C., and the step of adding and dissolving ketamine or a salt thereof to and in the solution obtained in step i), is at a temperature between +15° C. and +25° C.

17. A pharmaceutical composition consisting of the formulation as claimed in claim 1.

* * * * *